United States Patent [19]

Tiers et al.

[11] 3,974,147

[45] Aug. 10, 1976

[54] REDUCED STYRYL DYES

[75] Inventors: George V. D. Tiers; Joseph A. Wiese, Jr., both of St. Paul, Minn.

[73] Assignee: Minnesota Mining and Manufacturing Company, St. Paul, Minn.

[22] Filed: June 25, 1975

[21] Appl. No.: 590,321

Related U.S. Application Data

[63] Continuation-in-part of Ser. No. 347,193, April 2, 1973, Pat. No. 3,916,069.

[52] U.S. Cl. .............................. 260/240 D; 96/1.6; 96/129; 250/475; 260/240.9; 260/326.11 R; 427/151; 427/261

[51] Int. Cl.² .............. C07D 401/06; C07D 405/06; C07D 413/06

[58] Field of Search ......... 260/240.9, 240 D, 326.11

[56] References Cited

UNITED STATES PATENTS

| | | | |
|---|---|---|---|
| 3,576,801 | 4/1971 | Brinkhoff | 260/240 D |
| 3,796,573 | 3/1974 | Jones | 96/106 |

OTHER PUBLICATIONS

Hamer The cyamine Dyes and Related Compounds Interscience, N. Y., N. Y., 1964 pp. 306–308.

Kuhn et al., Chem. Berichte 65 (1932) p. 1.

*Primary Examiner*—Arthur P. Demers

*Attorney, Agent, or Firm*—Alexander, Sell, Steldt & DeLaHunt

[57] ABSTRACT

Dihydroheterocyclic amines having a N-hydrocarbyl substitution and a 2-(or 4-) (omega-(nuclearly substituted cyclic)) vinylenyl substitution are described. There compounds are oxidized in an acidic environment to produce styryl dyes.

12 Claims, 103 Drawing Figures

REDUCED STYRYL DYES

Figure 1:
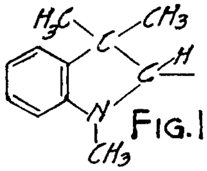
Figure 2:
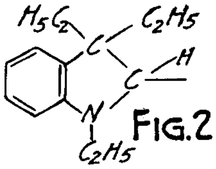
Figure 3:
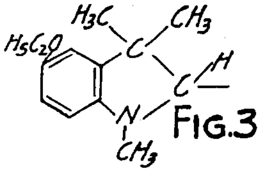
Figure 4:
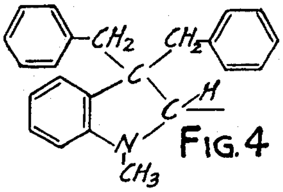

This application is a continuation-in-part divided from application Ser. No. 347,193 filed April 2, 1973, now U.S. Pat. No. 3,916,069.

The present invention relates to derivatives of dihydroheterocyclic amines which are N-heterocycles in which the nitrogen and one other member are in a reduced state. More particularly, it relates to N-hydrocarbyl-substituted dihydroheterocyclic amines having a 2-(or 4-) omega-(nuclearly substituted cyclic)vinylenyl substituent and to processes for the preparation of such amines.

The N-hydrocarbyl-substituted dihydroheterocyclic amines of the invention are substantially colorless but when oxidized in an acidic environment yield compounds exhibiting practically any desired color of the visible spectrum depending on the choice of substituents in the molecule. The N-hydrocarbyl-substituted dihydroheterocyclic amines of the invention find utility in radiation-sensitive elements as described and claimed in U.S. Pat. Nos. 3,856,552 and 3,916,069 (S.N. 347,193).

Non-silver radiation-sensitive elements in which colored images are produced on exposure of the element to various kinds of radiation have been described. Such elements generally contain one or more color progenitors, which form color on protonation, in combination with an acid progenitor. Thus, in U.S. Pat. Nos. 2,474,084; 2,505,470 and 2,983,756, there are described light-sensitive elements containing as the color progenitor leuco or carbinol bases of tri-phenylmethane or diphenyl-methane dyes. These elements produce colorations limited mainly to the blue to green range of the visible spectrum. In U.S. Pat. No. 3,102,810, there are described light-sensitive elements containing as the color progenitor one or more styryl or leuco dye bases. These latter elements produce colorations generally limited to the yellow to red range of the visible spectrum.

Elements containing the above described color progenitors, although providing colors that are generally dense and relatively stable, tend to develop color on storage even in the absence of radiation. Furthermore, the backgrounds of elements that have been imaged tend to deteriorate and to develop color on storage. This is disadvantageous as to the stability of the image.

It has now been found that N-hydrocarbyl dihydroheterocyclic amines having a vinylenyl substituent in the 2-(or 4-) position which has a nuclearly substituted cyclic group in the omega (distal) positions are color progenitors which when oxidized in an acidic or anionogenic environment yield colored products exhibiting practically any desired color of the visible spectrum depending on the choice of additional substituents.

The term "hydrocarbyl" will be understood herein as a monovalent radical of 1 to 10 carbon atoms and hydrogen, including alkyl, cycloalkyl, phenyl and benzyl and including not more than about 60 atomic weight units, i.e., daltons, of the elements O, N, F, Cl or S.

O, N and S may be in chains as hydroxyethyl, ethoxyethyl, dimethyaminoethyl, 3-thia pentyl, or the like or in cyclic structures as morpholino, piperidino, thiazino or the like. Hydrogen atoms are usually simple substituents.

The term dihydroheterocyclic amine refers to a nitrogen heterocycle in which the nitrogen and one other atom (usually adjacent) are in a reduced state as indolenine is related to refer particularly to fully unsaturated cyclic structures as phenyl, pyridine, pyrrole, furan, thiophene and that reduced forms will in general be named appropriately.

In radiation sensitive elements containing anionogens, these color progenitors are storage stable for all practical purposes indefinitely (i.e., the element does not develop color in areas that have not been exposed to suitable radiation). More specifically, the amines of the invention are essentially colorless N-hydrocarbyl-substituted-2-or 4-) (omega-(nuclearly substituted cyclic)vinylenyl) dihydroheterocyclic amines. These may frequently be referred to herein as substituted heterocyclic amines or as vinylenyl-substituted heterocyclic amines. They may also be called 2-(or 4-) (omega-(nuclearly substituted cyclic)) vinylenyl N-hydrocarbyl dihydronitrogen heterocycles. On oxidation in an acidic environment, there heterocyclic amines produce styryl dyes, The substituted dihydroheterocyclic amines of the invention have a dihydroheterocyclic nucleus joined at its 2- or 4- position to an auxochromically substituted cyclic nucleus either directly or through divalent linking chain of 1 to 5 methinyl groups. These amines may be represented by two general structures:

$D—(CH=CH)_n—CH=CAA'$ Structure I or $D—(CH=CH)_n—A$ Structure II

It will be seen that structures I and II differ in that the methinyl group to which A is attached is further substituted by A' in Structure I. In Structures I and II, n is an integer from 1–3 and D is a dihydroheterocyclic nucleus, represented by one or the other of the structural variations shown as Structure III. The free valences in the vinylenyl groups are usually attached to H but one may be attached to hydrocarbyl, preferably methyl, ethyl or phenyl.

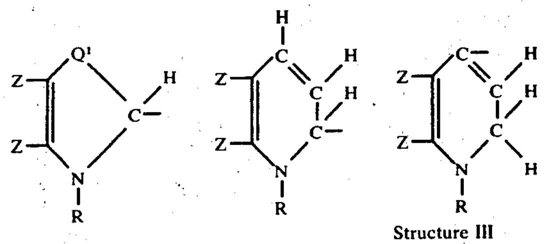

Structure III

In Structure III, R is hydrocarbyl and preferably primary alkyl of 1–6 carbon atoms, $Q^1$ is $CR^1R^1$, S O, Se or NR in which each $R^1$ is H or hydrocarbyl selected from the group consisting of alkyl of 1 to 6 carbon atoms, phenyl and benzyl and preferably is methyl and the two Z groups may be individually hydrogen atoms or together may be either a benzo- or naptho- substituent with or without auxochromic substituents which, substituted on phenyl or heterocyclic nuclei herein, include aryl, alkyl, dialkylamino, dialkylsulfonamido, alkylsulfonyl, arylsufonamido, alkoxy, aryloxy, nitro, cyano, alkoxycarbonyl and halogen as well as divalent benzo or naphthaleno groups, but any group which is compatible with synthetic methods employed and influences the absorption spectrum of the oxidized compound may be employed. It is convenient to designate the two methinyl groups nearest the A groups, which methinyl groups form a vinylenyl group, as the proximal and anteproximal methinyl groups. With respect to the dihydroheterocyclic nucleus, they are respectively distal and antedistal or ultimate and penultimate.

In Structures I and II, A and A' are independently monovalent cyclic nuclei having one of the structural variations designated as Structure IV.

Structure IV

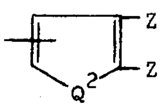

or

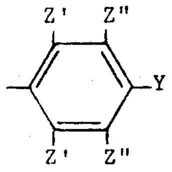

In Structure IV, R and the two Z's are as defined above. $Q^2$ is O, S, Se, NH or NR; Y is H, Cl, F, Br, alkyl of 1–6 carbon atoms OH, $OR^2$, $SR^5$ or $NR^3R^4$;

Z' is H, Cl, F, Br, alkyl of 1–6 carbon atoms, $OR^5$ or $NR_2^5$;

Z'' is H, Cl, F, Br, alkyl of 1–6 carbon atoms or $OR^5$;

Z' and adjacent Z'' taken together can be benzo or naptho with or without auxochromic substituents;

$R^2$ is alkyl of 1–6 carbon atoms;

$R^5$ is methyl or ethyl;

$R^3$ and $R^4$ are independently hydrocarbyl or taken together with an adjacent Z'' each can be independently 1,2-ethylene, 1,3-propylene or 1,2-phenylene or in conjunction with each other can form a 5 or 6 membered ring including not more than one oxygen or one additional nitrogen. In Structure I, when A and A' are taken together with the carbon to which attached they may form a xanthone or fluorenone structure.

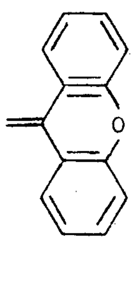

or

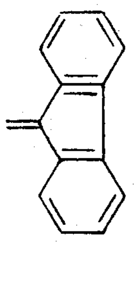

Examples of suitable dihydroheterocyclic nuclei or radicals (Structure III) that may be present in the substituted dihydroheterocyclic amine of the invention include those shown in FIGS. 1 to 29 inclusive, wherein the names of the respective structures are:

| Figure | Name |
|---|---|
| 1 | 1,3,3-trimethyl-2,3-dihydro-2-indolyl |
| 2 | 1,3,3-triethyl-2,3-dihydro-2-indolyl |
| 3 | 5-ethoxy-1,3,3-trimethyl-2,3-dihydro-2-indolyl |
| 4 | 1-methyl-3,3-dibenzyl-2,3-dihydro-2-indolyl |
| 5 | 5-chloro-1,3,3-trimethyl-2,3-dihydro-2-indolyl |
| 6 | 5-phenyl-1,3,3-trimethyl-2,3-dihydro-2-indolyl |
| 7 | 5-diethylamino-1,3,3-trimethyl-2,3-dihydro-2-indolyl |
| 8 | 5-benzene sulfonyl-1,3,3-trimethyl-2,3-dihydro-2-indolyl |
| 9 | 5-ethoxycarbonyl-1,3,3-trimethyl-2,3-dihydro-2-indolyl |
| 10 | 5-dimethylamino carbonyl-1,3,3-trimethyl-2,3-dihydro-2-indolyl |
| 11 | 5-cyano-1,3,3-trimethyl-2,3-dihydro-2-indolyl |
| 12 | N-butyl-2,3-dihydro-2-quinolyl |
| 13 | 6-bromo-1-phenyl-1,2-dihydro-2-quinolyl |
| 14 | 6-ethoxy-1-ethyl-1,2-dihydro-2-quinolyl |
| 15 | 1-ethyl-1,2-dihydro-2-(5-benzo)-quinolyl |
| 16 | 3-ethyl-2,3-dihydro-2-benzoxazolyl |
| 17 | 6-methoxy-3-ethyl-2,3-dihydro-2-benzoxazolyl |
| 18 | 3-methyl-2,3-dihydro-2-benzothiazolyl |
| 19 | 6-chloro-3-n-propyl-2,3-dihydro-2-benzothiazolyl |
| 20 | 6-phenoxy-3-ethyl-2,3-dihydro-2-benzothiazolyl |
| 21 | 6-methyl-3-phenyl-2,3-dihydro-2-benzothiazolyl |
| 22 | 6-dimethylaminosulfonyl-3-ethyl-3,3-dihydro-2-benzothiazolyl |
| 23 | 3-butyl-2,3-dihydro-2[2,1,d]-naphththothiazolyl |
| 24 | 3,5,6-trimethyl-2,3-dihydro-2-benzothiazolyl |
| 25 | 3-cyclohexyl-2,3-dihydro-2-benzothiazolyl |
| 26 | 1,3-dimethyl-1,2-dihydro-2-benzimidazolyl |
| 27 | 5-methoxy-1,3-diethyl-1,3-dihydro-2-benzimidazolyl |
| 28 | 3-ethyl-2,3-dihydro-2-benzoselenazolyl |
| 29 | 6-methoxy-3-ethyl-2,3-dihydro-2-benzoselenazolyl |

The substituted dihydroheterocyclic nuclei D of Structures III, exemplified in FIGS. 1–29, are attached to cyclic nucleus A (cf. Structure II) by a divalent chain having 2, 4 or 6 methinyl groups, including as examples:

—CH═CH—, —CH═CH—CH═CH—,
—CH═CH—CH═CH—CH═CH—.

Examples of suitable nuclei A, Structure IV heterocyclic radicals, include those shown in FIGS. 30 to 58 inclusive wherein the names associated with the respective structures are:

| Figure | Name |
|---|---|
| 30 | 2-pyridyl |
| 31 | 4-quinolyl |
| 32 | 2-benzothienyl |
| 33 | 1-methyl-2-benzimidazolyl |
| 34 | 2-benzoxazolyl |
| 35 | 3-furyl |
| 36 | 3-thienyl |
| 37 | 2-thienyl |
| 38 | 1-ethyl-3-pyrryl |
| 39 | 1-methyl-2-pyrryl |
| 40 | 1-methyl-3-indolyl |
| 41 | 10-methyl-7-phenothiazinyl |
| 42 | 4-diethylamino-phenyl |
| 43 | 4-dimethylamino-α-naphthyl |
| 44 | 2-dimethylamino-5-methyl-phenyl |
| 45 | 4-morpholinyl-phenyl |
| 46 | p-anisyl |
| 47 | p-hydroxyphenyl |
| 48 | o-butoxyphenyl |
| 49 | p-phenoxy-phenyl |
| 50 | biphenylyl |
| 51 | phenyl |
| 52 | α-naphthyl |
| 53 | 2-ethoxy-3-(diethylamino)-phenyl |

-continued

| Figure | Name |
|---|---|
| 54 | p-cyanophenyl |
| 55 | p-chlorophenyl |
| 56 | p-dimethylamino-sulfonyl |
| 57 | 2,4-dimethoxyphenyl |
| 58 | p-thioanisyl |

Figure 58:
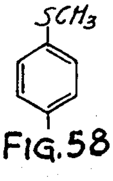

As described by the general structures, the vinylenyl-substituted heterocyclic amines of the invention have two structural parts illustrated in part in FIGS. 1–58. Illustrations of these structures are provided in FIGS. 59 through 101, the names of the respective compounds of which are given below.

| Figure | Name |
|---|---|
| 59 | 2-(4-(dimethylamino)styryl)-1,3,3-trimethylindoline |
| 60 | 2-(2-chloro-4-dimethylaminostyryl)-1,3,3-trimethyl-indoline |
| 61 | 2-(4-diethylaminostyryl)-1,3,3-trimethylindoline |
| 62 | 2-(4-morpholinostyryl)-1,3,3-trimethylindoline |
| 63 | 2-(3,4-dimethoxy styryl)-1,3,3-trimethylindoline |
| 64 | 2-(4-(ethylbenzylamino)styryl)-1,3,3-trimethylindoline |
| 65 | 2-(3,5-di-t-butyl-4-hydroxystyryl)-1,3,3-trimethyl-indoline |
| 66 | 2-(2,3-benzostyryl)-1,3,3-trimethylindoline |
| 67 | 2-(2-dimethylamino-5-methyl-styryl)-1,3,3-trimethylindoline |
| 68 | 2-(4-(phenylmethylamino)styryl)-1,3,3-trimethyl-indoline |
| 69 | 2-(4-bis(2-chloroethyl)amino styryl)-1,3,3-trimethylindoline |
| 70 | 2-(4-hexyloxystyryl)-1,3,3-trimethylindoline |
| 71 | 2-(2-ethoxy-4-diethylaminostyryl)-1,3,3-trimethyl-indoline |
| 72 | 2-(4-dibenzylaminostyryl)-1,3,3-trimethylindoline |
| 73 | 2-(2-methyl-4-(benzylethylamino)styryl)-1,3,3-trimethylindoline |
| 74 | 2-(2-(9-ethyl-3-carbazolyl)ethenyl)-1,3,3-trimethyl-indoline |
| 75 | 2-(2-(N-methyl-2-pyrryl)ethenyl)-1,3,3-trimethyl-indoline |
| 76 | 2-(2-(N-benzyl-3-indolyl)ethenyl)-1,3,3-trimethyl-indoline |
| 77 | 2-(2-thienyl-ethenyl)-1,3,3-trimethylindoline |
| 78 | 2-(2-pyrryl-ethenyl)-1,3,3-trimethylindoline |
| 79 | 2-(4-(4-dimethylaminophenyl))butadienyl-1,3,3-trimethylindoline |
| 80 | 2-(4,4-bis(4-dimethylaminophenyl)butadienyl)-1,3,3-trimethylindoline |
| 81 | 4-(4-dimethylaminophenyl-styryl)-N-ethyl-1,2-dihydro-pyridine |
| 82 | 4-(4-(4-dimethylaminophenyl)butadienyl)-N-ethyl-1,2-dihydropyridine |
| 83 | 4-(4,4-bis(4-dimethylaminophenyl)butadienyl)-N-ethyl-1,3-dihydropyridine |
| 84 | 2-(4-dimethylaminostyryl)-N-ethyl-1,2-dihydro-quinoline |
| 85 | 2-(4-(4-dimethylaminophenyl)butadienyl)-N-ethyl-1,2-dihydroquinoline |
| 86 | 2-(4,4-bis(4-dimethylaminophenyl)butadienyl)-N-ethyl-1,2-dihydroquinoline |
| 87 | 2-(4,4-bis(4-dimethylaminophenyl)butadienyl)-4-methyl-N-ethyl-1,2-dihydroquinoline |
| 88 | 2-(4-dimethylaminophenyl)styryl-N-ethyl-2,3-dihydro-benzoxazole |
| 89 | 2-(4-(4-dimethylaminophenyl)butadienyl)-N-ethyl-2,3-dihydro-benzoxazole |
| 90 | 2-(4,4-bis(4-dimethylaminophenyl)butadienyl)-N-ethyl-5-carbethoxy-3,3-dimethyl-indoline |
| 91 | 2-(4-dimethylaminophenyl)-styryl-N-ethyl-2,3-dihydro-benzothiazole |
| 92 | 2-(4-bis(4-dimethylaminophenyl)butadienyl)-NO ethyl-2,3-dihydrobenzothiazole |
| 93 | 2-(4-dimethylamino styryl)-N-ethyl-2,3-dihydro-naphthothiazole |
| 94 | 2-(4-(4-dimethylaminophenyl)butadienyl-N-ethyl-2,3-dihydronaphthothiazole |
| 95 | 2-(4,4-bis(4-dimethylaminophenyl)butadienyl)-N-ethyl-2,3-dihydronaphthothiazole |
| 96 | 2-(4,4-bis(4-dimethylaminophenyl)butadienyl)-1,3,3-trimethyl-5-carbonamidoindoline |
| 97 | 2-(4,4-bis(4-dimethylaminophenyl)butadienyl)-1,3,3-trimethyl-5-cyanoindoline |
| 98 | 2-(4,4-bis(4-dimethylaminophenyl)butadienyl)-1,3,3-trimethyl-5-methylsulfonylindoline |
| 99 | 2-(4,4-bis(4-dimethylaminophenyl)butadienyl)-1,3,3- |

-continued

| Figure | Name |
|---|---|
| | trimethyl-5-dimethylsulfonamidoindoline |
| 100 | 2-(4,4-bis(4-dimethylaminophenyl)butadienyl)-1,3,3-trimethyl-5-ethoxyindoline |
| 101 | 2-(4,4-bis(4-dimethylaminophenyl)butadienyl)-1,3,3-trimethyl-5-nitroindoline |

The preferred substituted dihydroheterocyclic amines are those amines which are defined as N-(lower alkyl)-substituted-2-(or 4-) [(omega-dihydrocarbyl-aminocyclic)vinylenyl]dihydroheterocyclic amines. These substituted dihydroheterocyclic amines are preferred because on acid oxidation, they yield dyes having deep tinctorial strength, i.e., a 1 mil (25 micron) thick resin coating containing 1 part by weight of dye per 10 parts by weight of colorless resin has an optical density of at least 1. Because of their stability toward adventitious discoloration, the preferred dihydroheterocyclic amines of the invention are those of Structure II above wherein cyclic nucleus A has the Structure IV as follows:

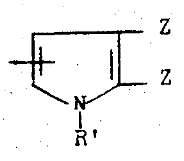

, and

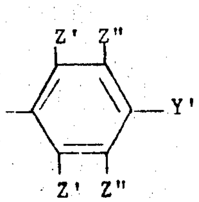

wherein R′, Z, Z′, Z″ are as defined above and Y′ is $NR^6R^7$,

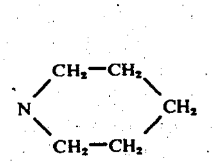

or

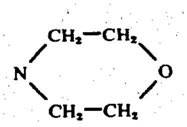

wherein $R^6$ and $R^7$ are hydrocarbyl.

Figure 102:
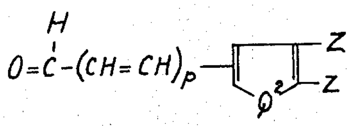
Figure 103:
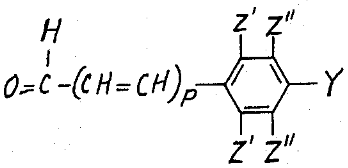

The substituted dihydroheterocyclic amines of the invention are conveniently prepared by the reduction of a corresponding dye. Thus, the substituted dihydroheterocyclic amines of Structure II are obtained by the reduction of styryl dyes. Styryl dyes which are precursors for the substituted heterocyclic amines of Structure II may be prepared in one procedure by condensation of an N-heterocyclic quaternary salt having a reactive group in the 4- or 2-position with aldehydes having the structures of FIGS. 102 and 103 wherein Z, Z′, Z″, Y′ and $Q^2$ are as defined before; p is 0 to 3. Other procedures are provided by V. Parameswaran et al., Indian Journal of Chemistry, Vol. 12, pp, 785–792 (August, 1974).

Figure 63:
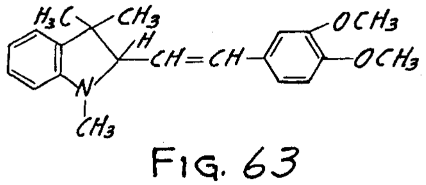
Figure 64:
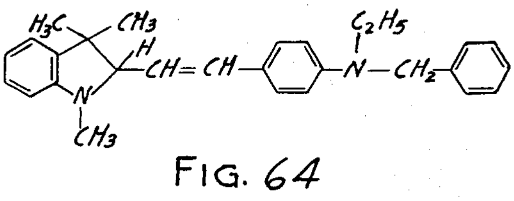
Figure 65:
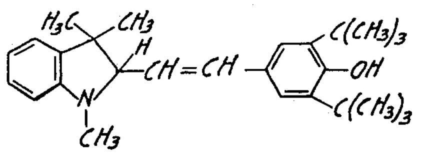
Figure 66:
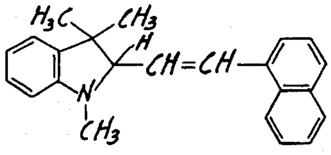
Figure 67:
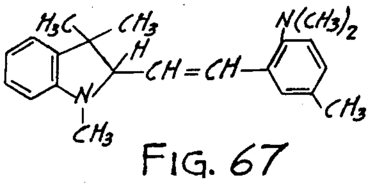
Figure 68:
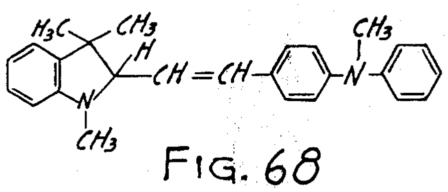
Figure 69:
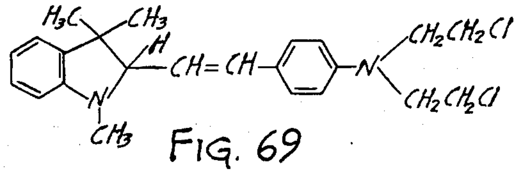
Figure 70:
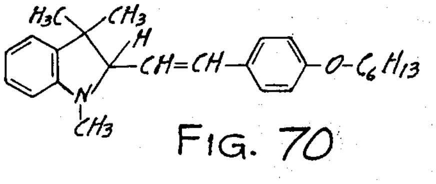
Figure 71:
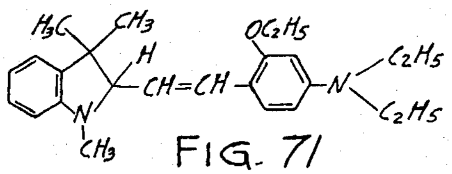
Figure 72:
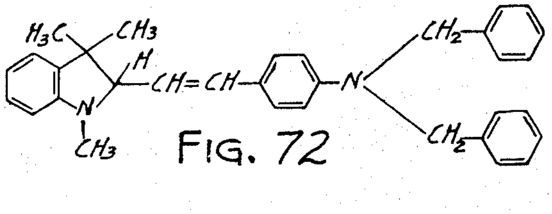
Figure 73:
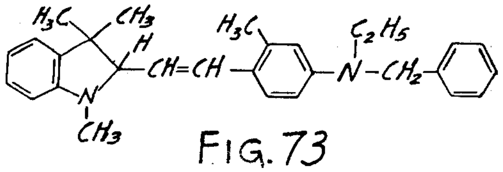
Figure 74:
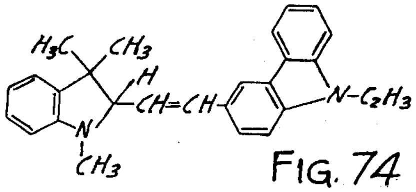
Figure 75:
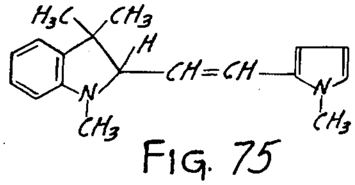
Figure 76:
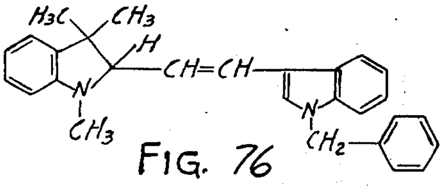
Figure 77:
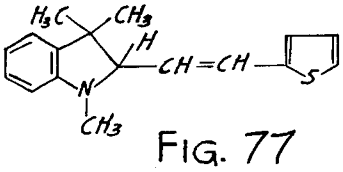
Figure 78:
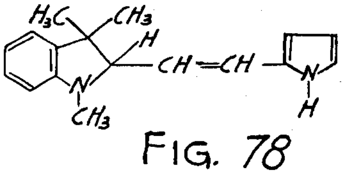

Other preferred dihydroheterocyclic amines of the invention which are preferred because of their yellow or orange colors are N-(lower alkyl)-substituted-2-(or 4-) [(omega-mono [or poly-]-alkoxy-cyclic) vinylenyl]dihydroheterocyclic amines as shown in FIGS. 63 and 70 or the N-(lower alkyl)-substituted -2-(or 4-) [(omega-heterocyclic)vinylenyl]dihydroheterocyclic amines, e.g., FIGS. 75 through 78.

The reduction of styryl dyes to the substituted heterocyclic amines of the invention is accomplished using any reducing agent having sufficient reducing power. A reducing agent has sufficient reducing power if, when added to a solution of the dye, it will discharge the dye color from the solution. One generally useful reducing agent is sodium borohydride. The reduction of the styryl dyes is carried out by the addition of the selected reducing agent in small portions to a solution of the dye in a solvent at a temperature of from about 0° to 50° C. allowing sufficient time between additions for the reducing agent to react before the next portion is added. No additional reducing agent is added after color is completely discharged from the dye solution. Preferably, the temperature is maintained at from about 15° to 30° C. in which range the reaction usually proceeds rapidly but with minimization of any tendency for the reduction of unsaturation in the dye molecule other than at the quaternized nitrogen. In producing the amine of the invention, sufficient reducing agent is required to provide 2 atoms of hydrogen per molecule of dye. Lesser amounts may be used where the dye is not pure and greater amounts may be required in some instances in a range of from about 1.8 to about 4 atoms of hydrogen per molecule of dye. It is desirable that the dye be of sufficient purity that the color is discharged after the addition of sufficient reducing agent to provide 1.9 to 2.1 atoms of hydrogen per molecule of dye.

Solvents in which the reaction may be carried out are those solvents in which the dyes are soluble and which are not reduced by the reducing agent at a rate appreciably faster than are the dyes. Examples of such solvents include water, aqueous alcohol, methanol, ethanol, acetone (the dyes reduce faster than does acetone) isopropanol, and the like. Generally, from 10 to 100 parts by volume of solvent per part by weight of dye is used depending on the solubility of the particular dye. It is often advantageous to carry out the reduction in a mixture of water and a water-immiscible solvent such as, for example, benzene, toluene, methylene chloride or chloroform because the amine is generally more soluble in the water-immiscible solvent.

The reduction is complete when color has been discharged from the dye solution. This generally requires from a minute or so to 3 or more hours depending on the amount and solubility of dye being reduced as well as on the solubility of the reducing agent and whether it is liquid or solid. Although quantities of several grams of dye in water may be reduced in a few minutes by aqueous solutions of sodium borohydride, quantities of 10 kg or more of dye may require 3 or more hours with the same reducing agent. Because the reaction is exothermic, it is advantageous to cool the reaction.

In addition to sodium borohydride, mentioned above as a reducing agent, suitable reducing agents include tetramethyl ammonium borohydride, sodium hydride, sodium amalgam, aluminum hydride, lithium aluminum hydride, sodium in alcohol, stannous chloride in alcohol, zinc and alcoholic hydrochloric acid, amalgamated tin and hydrochloric acid (care must be taken to exclude oxygen during the reaction and then to neutralize the acid with base immediately following the reaction). Some of these must be used under anhydrous conditions. Electrochemical reduction is also a suitable procedure.

Following the reduction reaction, the solution of crude substituted heterocyclic amine, if in a nonaqueous solvent, is conveniently diluted with water and extracted with several portions of a water insoluble solvent such as benzene, toulene, dipropylether, chloroform, methylene chloride, or the like. Methylene chloride is found to be especially convenient. The crude amine is recovered from the combined extracts and purified by recrystallization or by liquid chromatography.

The substituted heterocyclic amines of the invention find use in nonsilver photosensitive compositions and in elements or constructions utilizing these compositions which print out an image directly on exposure to suitable radiation as described and claimed in our parent application Ser. No. 347,193. Such compositions generally comprise at least one amine of the invention, an acid progenitor or anionogen in a suitable binder. An anionogen is a compound which is stable when exposed to normal room light, is soluble in the binder system, and provides an anion when exposed to a source of energy such as an electron beam. In a preferred composition, the binder is also the anionogen such as a polymer containing halogen. The composition may also contain additional components such as, for example, sensitizing compounds or dyes, fillers, plasticizers, or other modifiers all coated on a supporting film such as polyethylene terephthatate, or in a self-supporting film.

In the absence of sensitizing compound or dye, the compositions, including the heterocyclic amines of the invention, are insensitive to visible radiation, i.e., those radiations having a wavelength greater than about 4000A. Such compositions, contrary to prior art compositions are stable to storage, even in normal light, essentially indefinitely. However, they are somewhat sensitive to, and hence exposed by ultraviolet light, i.e., light having a wavelength substantially less than about 4000A as a result of formation of acid or much more readily by harder radiations such as are afforded by electron beams, X-rays, and other high energy radiation in the presence of anionogens. Many of the compositions are also sensitive to heat.

The dye progenitor compounds herein described by which will be understood the dihydroheterocyclic amines of the invention find particular utility in the preparation of normally stable image recording sheets on which images may be recorded directly by exposure to a suitably modulated electron beam; and in one aspect the invention therefore relates to the preparation and use of such sheet materials.

Sheet materials capable of being directly imaged by exposure to the electron beam have been previously described. The sheets of U.S. Pat. No. 3,370,981 are initially colored, being converted to a different color by the action of the beam. They do not provide a colorless background and accordingly cannot be combined in multiple-color packs to provide true color reproduction. U.S. Pat. No. 3,425,867 uses colorless materials but the colored product obtained on treatment is unstable and the color soon fades.

In forming and using the recording sheets of the present invention, a transparent, translucent, or opaque substrate is coated with a polymeric binder containing an electron beam sensitive colorless dye progenitor. An electron beam impinging on such a sheet produces a permanent image immediately and does not require fixing. Positive or negative images of a copy and full color copies can be made. Color correction is easy and enhancement of any given color is possible. Additional images may be added to a previously imaged sheet.

The electrical characteristics of the substrate are of considerable importance in the preparation of the recording sheets. If the dielectric constant is high enough (e.g., above about 5.0), no conductive coating is required. If the dielectric constant is lower (e.g., below about 5.0), then a conductive coating is required. If the substrate has a dielectric constant below about 5.0, then a conductive coating must be laid down on the substrate so that the resistivity will be less than $10^8$ ohm-cm.

By interaction with an electron beam, the progenitors yield cationic dyes which are intensely colored and transparent. A source of anion, which is referred to as an anionogen, must be available in order to allow formation of the colored form. The anionogenic function can come from the dye molecule, from the binder or from an additive in the binder-dye progenitor system.

The anionogen is a required component, and may come from the dye progenitor or precursor molecule, the binder, or an additive.

Figure 60:
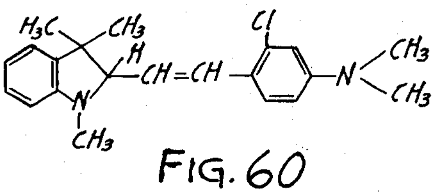
Figure 61:
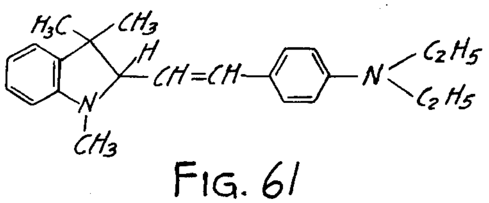

For example, the dye progenitor of FIG. 60 itself serves as an anionogen by virtue of the ring-substituted halogen atom. The compound is colorless and may be incorporated into a neutral binder (e.g., ethylcellulose, polyvinyl acetate, styrene-acrylonitrile copolymer). Upon exposure to an electron beam, a magenta image is produced immediately in the areas struck by the electron beam at about $10^{13}$ to $10^{14}$ electrons/cm$^2$.

The anionogen must be a compound which is stable to normal room light, soluble in the binder system, and able to provide an anion upon interaction with the electron beam. Halogen-containing compounds which provide a halide ion by interaction with the electron beam are useful. They include:

polyvinyl chloride
p-diiodobenzene
4,4'-dibromobiphenyl
1,2,4,5-tetrabromobenzene
4,4'-dibromodiphenyl ether
1,3,6,8-tetrachloropyrene
hexachloro diphenyl oxide
polybromotrifluoroethylene fluid
polychlorotrifluoroethylene fluid
chlorinated biphenyl
tetrabromomethyl methane
p-phenoxybenzenesulfonylfluoride Full color positive or negative copies of colored transparencies or hard copy can be prepared using the sheet material of this invention. The material to be copied is mounted in a convenient position and a video camera is focused on the material. The image viewed by the video camera may be monitored by a color TV monitor and the signal from the camera is fed into the electron beam recorder. For full color copies, color filters are sequentially placed before the video camera to provide color separation and the sheet material containing appropriate dye progenitor is used sequentially in the electron beam recorder. Finally, the three exposed sheets are laminated in register to form the full color transparency.

The invention is further illustrated by the following non-limiting examples in which all parts are by weight and temperatures in degrees centigrade unless otherwise indicated.

EXAMPLE 1

Figure 59:
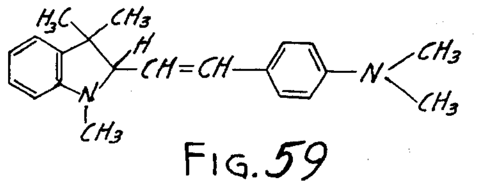

The substituted heterocyclic amine of FIG. 59, 2(4-dimethylaminostyryl)-1,3,3-trimethylindolenine, is prepared by the dropwise addition of a solution of 1 part of sodium borohydride in 10 parts of water to a stirring mixture of 30 parts of methylene chloride and 40 parts of an aqueous solution containing 2 parts of the styryl dye, 2(4-dimethylamino-styryl)-1,3,3-trimethylindolinium chloride. The addition of borohydride solution is continued until the color is fully discharged from the dye solution. The stirring is stopped, the phases separated, and the lower nonaqueous phase washed several times with several parts of water. The washed phase is then dried over anhydrous sodium sulfate (about 2 parts) and the methylene chloride distilled off. The residue obtained is recrystallized from methanol and yields the desired amine having a melting point of 124.5°– 126°C. Data from high resolution mass spectrography establish the molecular formula of the purified substituted heterocyclic amine as $C_{21}H_{26}N_2$.

EXAMPLE 2 (FIG. 60)

The substituted heterocyclic amine of FIG. 60, 2(2-chloro-4-dimethylaminostyryl)-1,3,3-trimethylindolenine is prepared by following the procedure of Example 1 with the substitution of the styryl dye 2(2-chloro-4-dimethylaminostyryl)-1,3,3-trimethylindolinium chloride for that used above. The desired amine is obtained with a melting point of 153.5°– 155.5°C., molecular formula by high resolution mass spectrography: $C_{21}H_{25}N_2Cl$.

The analogous heterocyclic amine 2(3-bromo-4-dimethylaminostyryl)-5-chloro-1,3,3-trimethylindolenine is also prepared and found to have a melting point of 85° – 87°C. The corresponding dyestuff is also magenta.

In the same way 2(2,4-dimethoxystyryl)-1,3,3-trimethylindolenine is prepared and found to have a melting point of 131°–134°C. The corresponding dyestuff is yellow.

EXAMPLE 3 (FIG. 62)

Figure 62:
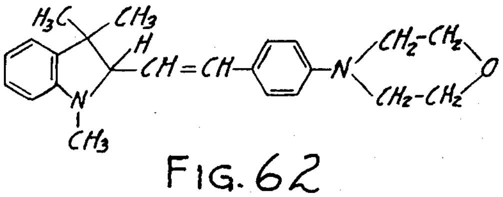

The heterocyclic amine of FIG. 62, (2-(4-morpholinostyryl)-1,3,3-trimethylindoline) is obtained by replacing the styryl dye used in the procedure of Example 1 with the styryl dye, 2(4-morpholinostyryl)-1,3,3-trimethylindolinium chloride. The desired amine is obtained as a partially purified material having a melting point of 121°–131°C. and an empirical formula of $C_{23}H_{28}ON_2$.

EXAMPLE 4 (FIG. 80)

Figure 80:
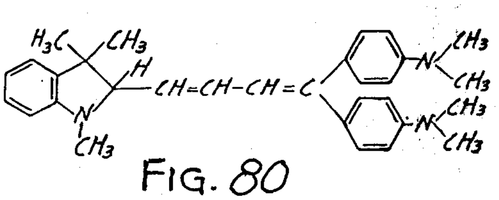
Figure 81:
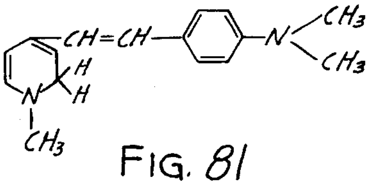
Figure 82:
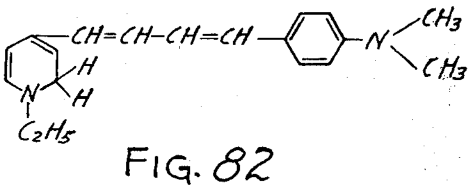
Figure 83:
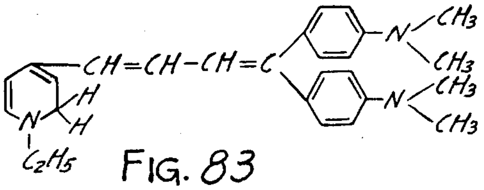
Figure 84:
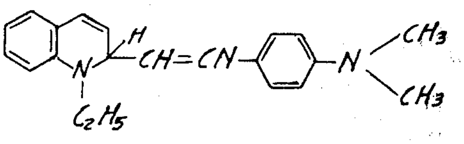
Figure 85:
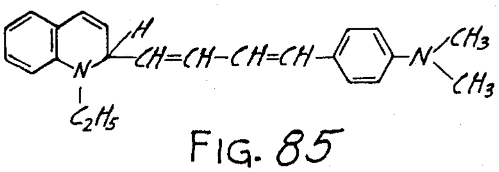
Figure 86:
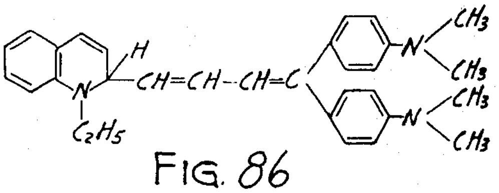
Figure 87:
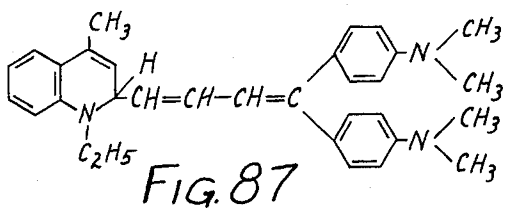
Figure 88:
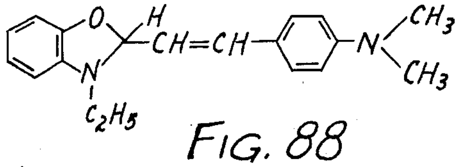
Figure 89:
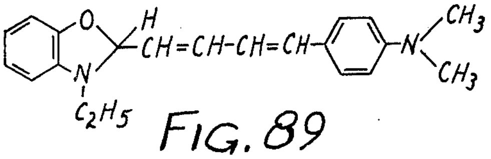
Figure 90:
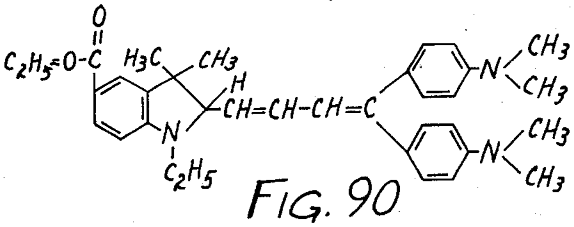
Figure 91:
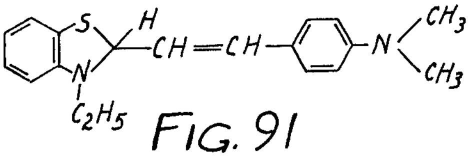
Figure 92:
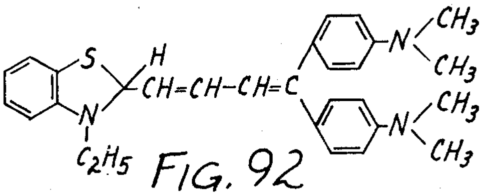
Figure 93:
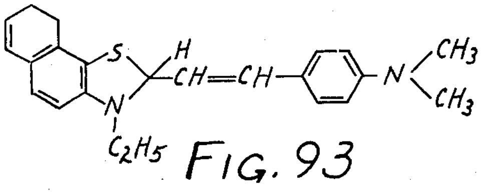
Figure 94:
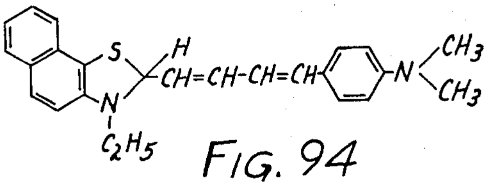
Figure 95:
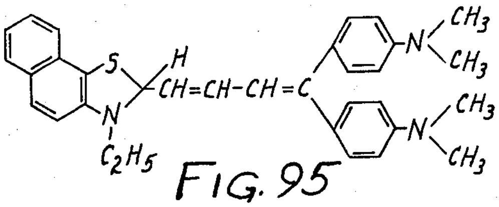
Figure 96:
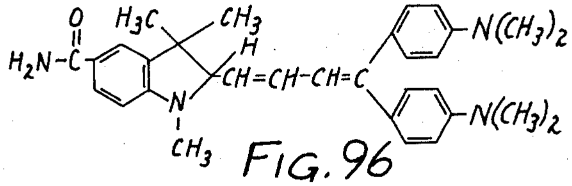
Figure 97:
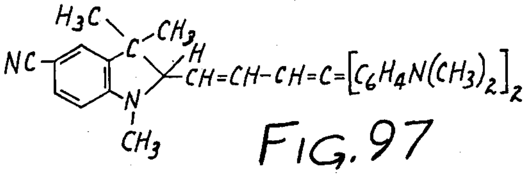
Figure 98:
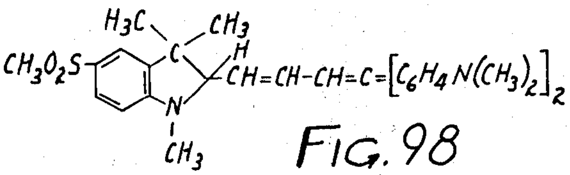
Figure 99:
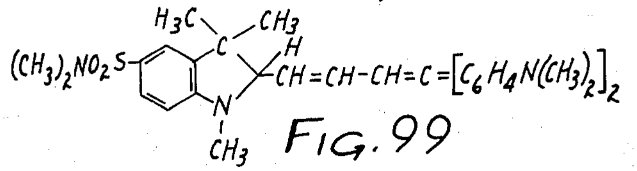
Figure 100:
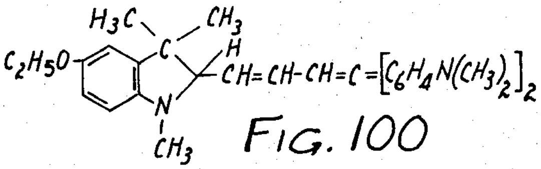
Figure 101:
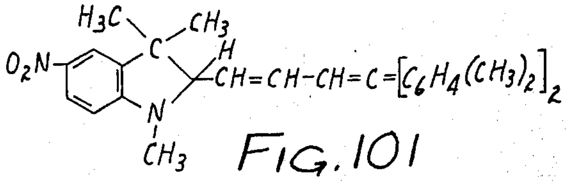

The substituted heterocyclic amine of FIG. 80, (2-(4,4-bis(4-dimethylaminophenyl)butadienyl)-1,3,3-trimethylindoline is prepared by dropwise addition of a solution of 1.1 parts of sodium borohydride in 13 grams of water to a stirring mixture of 4.86 grams (0.01 moles) of the styryl dye, 2(4,4-bis(4-dimethylamino-phenyl)-butadientyl)-1,3,3-trimethylindolinium chloride in 100 grams of water and 37 grams of methylene chloride. After 4.6 grams of the sodium borohydride solution has been added, the blue color of the styryl dye is fully discharged. The methylene chloride layer is separated, dried over sodium sulfate and the methylene chloride distilled off in a rotary evaporator. The dark brown residue is milled in 95% ethanol containing about 0.1 parts of sodium borohydride and then filtered. After vacuum drying, the tan colored insolution portion weights 3.25g, sinters at 172°C. and melts at 182°–183°C. The molecular formula of the purified substituted heterocyclic amine is found to be $C_{31}H_{37}N_3$.

EXAMPLE 5

In a suitable container equipped with an air condenser and a drying tube to exclude atmospheric moisture and heated by a steam bath, are placed 50 parts glacial acetic acid, 2 parts of concentrated hydrochloric acid, 7.07 parts of 3,3-bis(4-dimethylaminophenyl-)acrolein (0.024 moles) and 4.16 parts of 1,3,3-trimethyl-2-methylene-indoline (0.024 moles). The mixture is heated for 18 hours during which time it takes on a deep blue coloration. The solution is concentrated to about one-half its initial volume, diluted to 600 parts by volume with water and salted out with a mixture of sodium chloride and sodium acetate. After filtering and drying, the solid is extracted with chloroform in a Soxhlet extractor to remove salt and the chloroform concentrate evaporated to yield 11.7 parts of green-grey microcrystals of 2-(4,4-bis-(4-dimethylaminophenyl)butadienyl)-1,3,3-trimethylindolinium chloride.

Figure 79:
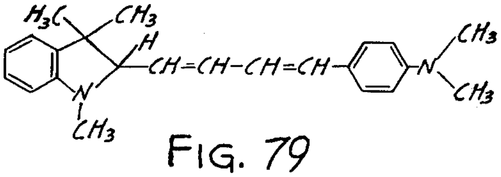

The above indolinium chloride is used in place of the styryl dye of Example 1 to give the heterocyclic amine of FIG. 79.

EXAMPLE 6

The substituted heterocyclic amines shown in FIGS. 59–95 are prepared by the dropwise addition of a solution of 1 part of sodium borohydride in 20 parts of ethanol to a solution of 1 part of the corresponding methine dye in 100 parts of methanol. The addition of borohydride solution is continued until the color is discharged from the dye solution. The methanol is evaporated from the reaction mixture and the residue taken up in about 20 parts methylene chloride. The supernatant solution is decanted from the insoluble residue formed on standing and is evaporated. The essentially colorless substituted heterocyclic amine obtained as a residue by evaporation of the methylene chloride is added to 100 parts of a 10% weight per weight solution of a copolymer of 87% vinyl chloride, 13% vinyl acetate (Bakelite VYHH) in 75/25 methyl ethyl ketone/toluene by weight to form a coating composition. The coating composition is coated at a wet thickness of 3 mils (75 microns) onto a transparent electrically conductive polyester film and dried. Samples of the coated sheet are exposed to a conventional electron beam at 20 kilovolts and 3 microamperes. Color of the developed image, and sensitivity, are given in Table 1.

Table 1

| Compound of Figure | Color | Sensitivity[a] |
|---|---|---|
| 59 | Magenta | A |
| 60 | Magenta | A |
| 61 | Magenta | A |
| 62 | Red-magenta | A |
| 63 | Yellow | C |
| 64 | Magenta | A |
| 65 | Orange | B |
| 66 | Amber | C |
| 67 | Yellow | D |
| 68 | Magenta | A |
| 69 | Scarlet | A |
| 70 | Yellow | C |

Table 1-continued

| Compound of Figure | Color | Sensitivity[a] |
|---|---|---|
| 71 | Magenta | A |
| 72 | Magenta | A |
| 73 | Magenta | A |
| 74 | Red-orange | A |
| 75 | Orange | A |
| 76 | Orange | A |
| 77 | Yellow | B |
| 78 | Yellow | A |
| 79 | Blue | B |
| 80 | Blue | A |
| 81 | Orange-yellow | A |
| 82 | Purple | A |
| 83 | Blue | A |
| 84 | Magenta | A |
| 85 | Blue | A |
| 86 | Blue | A |
| 87 | Blue | A |
| 88 | Yellow | D |
| 89 | Magenta | B |
| 90 | Blue | B |
| 91 | Magenta | C |
| 92 | Blue | B |
| 93 | Magenta | C |
| 94 | Magenta | C |
| 95 | Blue | B |

[a]Sensitivity
A = Good
B = Medium
C = Low
D = Insensitive

Those skilled in the art will readily perceive that numerous other dihydroheterocyclic amines of the invention can be obtained by the procedure herein disclosed and that they can be used similarly in radiation-sensitive compositions.

EXAMPLE 7

Transparent polyester film (2.5 mil or 0.0625 mm) was vapor coated with chromium to yield a sheet material with a resistivity of $10^4$ ohms per square and a visible light transmission of 50%. The conductive surface of the sheet was knife coated at a wet thickness of 3 mils or 0.075 mm with a solution of 50 mgm of the dihydroheterocyclic amine compound of FIG. 80 and 0.5 gm copolymer of 87% vinyl chloride — 13% vinyl acetate ("Vinylite VYHH") dissolved in 3.4 gm methylethylketone and 1.1 gm toluene.

The dihydroheterocyclic amine was dissolved in the polymer solution to form a clear colorless solution. After coating, the sheet was dried at room temperature to form a colorless transparent sheet which was stable in room light.

The sheet was exposed to a conventional electron beam using 20kV, 3$\mu$A. The film, upon exposure to the electron beam, immediately developed a transparent blue color. After removing the film from the electron beam assembly, the exposed portion of the film maintained its blue transparent color and the background remained clear, colorless and transparent. Unexposed film was stored in room light for an extended period of time without deleterious effect. The exposed film was also uniformly stable. Another portion of the prepared film was tested using an electron beam of 20kV, one square inch raster at from $10^{11}$ to $10^{14}$ electrons/cm$^2$. Variations in the optical density were achieved from visible marking at $10^{11}$ electrons/cm$^2$ to dense blue transparent image at $10^{14}$ electrons/cm$^2$. The unexposed film was stored in the laboratory under normal light conditions for about one-half year. This film was then exposed in the electron beam arrangement and the color developed immediately. A comparison with film which had been exposed to the electron beam one year before and allowed to remain in the laboratory under normal lighting showed no discernible difference.

Other color progenitor dihydroheterocyclic amines were substituted for that of FIG. 80 used above to produce equally effective electron beam recording sheets which produced images of other colors. Typical examples are as tabulated, the exposure in electrons/cm$^2$ required to produce an optical density of 1 being indicated for convenience.

| Compound (Figure) | Color | Exposure |
|---|---|---|
| 63 | Yellow | $10^{14}$ |
| 77 | Yellow | $10^{14}$ |
| 83 | Blue | $10^{14}$ |

EXAMPLE 8

In order to provide increased surface conductivity, a polyester film carrier was first coated with a dilute solution of polydimethyl dialkyl ammonium chloride ("Calgon 261"), and dried. The film was then further coated with the solution of binder and color precursor as in Example 7. The sheet had a resistivity of $10^4$ ohms/square and a light transmissivity approximately 97% of that of the uncoated polyester film. Under an electron beam exposure of $10^{14}$ electrons/cm$^2$ the sheet produced a blue transparent image.

EXAMPLE 9

The film base of Example 8 was coated with a solution of 0.5 g of styrene-acrylonitrile copolymer ("Tyril 880") and 50 mgm of the dihydroheterocyclic amine of FIG. 60 in 4.5 g of methyl isobutyl ketone. Exposure of the dried colorless sheet to the electron beam at 20kV and 3$\mu$A produced a transparent magenta image.

After removing the film from the electron beam assembly, the exposed portion maintained its magenta transparent color and the background remained clear, colorless and transparent even though it was left on an intensely lighted (600 watt) overhead projector for over four hours.

Similar results were obtained when the binder was replaced with:

A. VYHH applied as 10% solution in 3/1 mixture of methylethylketone and toluene.

B. 10% solution of polyvinyl acetate (Gelva V-100 from Shawinigan Products) in methylethylketone.

C. 3% solution of ethylcellulose in toluene (Ethocel N-200 from Dow Chemical Co.).

D. 10% solution of a chlorinated polyethylene containing 48% chlorine (QX 2243.25 from Dow Chemical) in methylethylketone.

Other materials which liberate anions on exposure to an electron beam and which serve as anionogens suitable for the purposes of the invention, such as those listed above, are also employed in making useful electron beam recording sheets.

EXAMPLE 10

Figure 5:
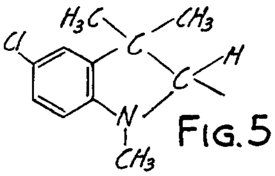
Figure 6:
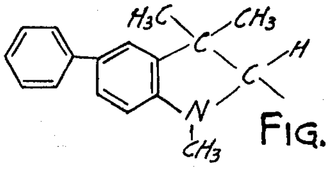
Figure 7:
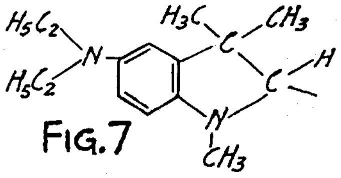
Figure 8:
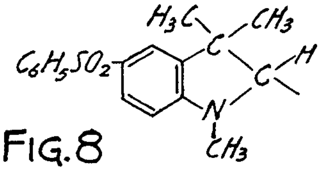
Figure 9:
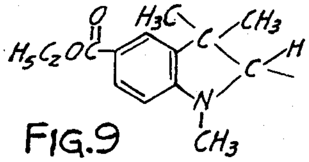
Figure 10:
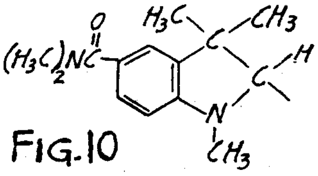
Figure 11:
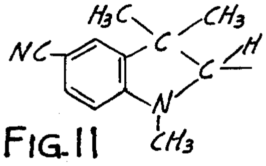
Figure 12:
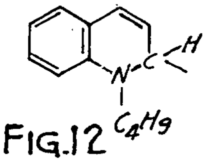
Figure 13:
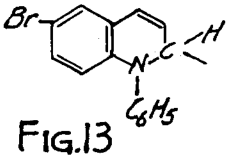
Figure 14:
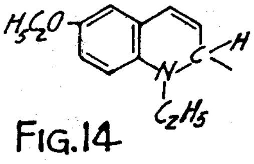
Figure 15:
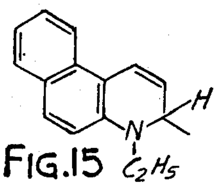
Figure 16:
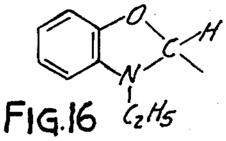
Figure 17:
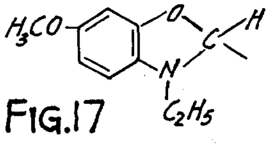
Figure 18:
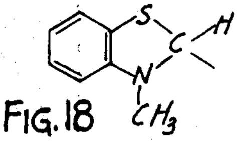
Figure 19:
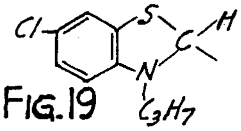
Figure 20:
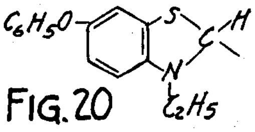
Figure 21:
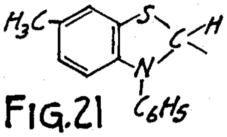
Figure 22:
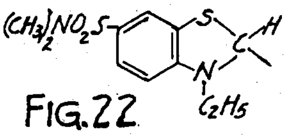
Figure 23:
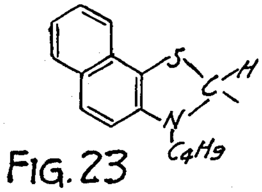
Figure 24:
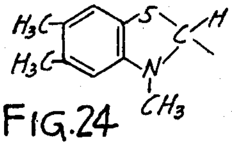
Figure 25:
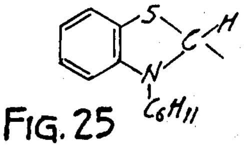
Figure 26:
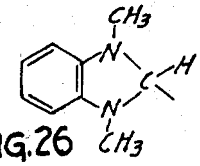
Figure 27:
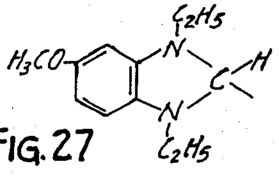
Figure 28:
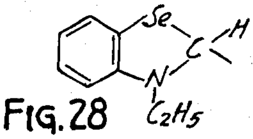
Figure 29:
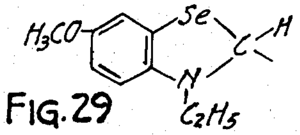
Figure 30:
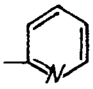
Figure 31:
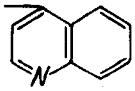
Figure 32:
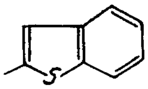
Figure 33:
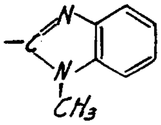
Figure 34:
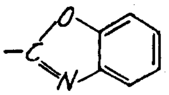
Figure 35:
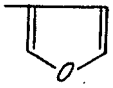
Figure 36:
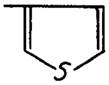
Figure 37:
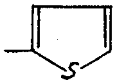
Figure 38:
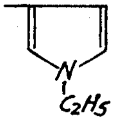
Figure 39:
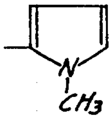
Figure 40:
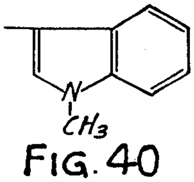
Figure 41:
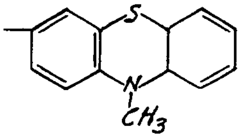
Figure 42:
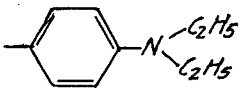
Figure 43:
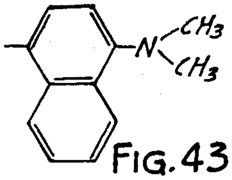
Figure 44:
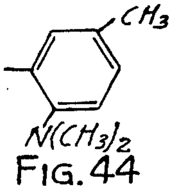
Figure 45:
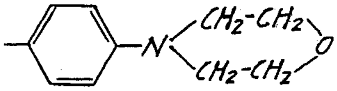
Figure 46:
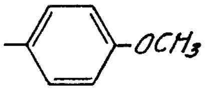
Figure 47:
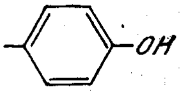
Figure 48:
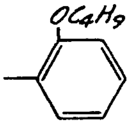
Figure 49:
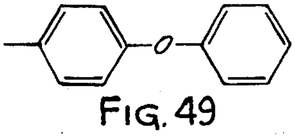
Figure 50:
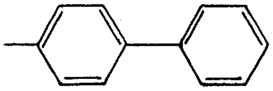
Figure 51:
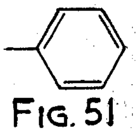
Figure 52:
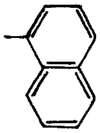
Figure 53:
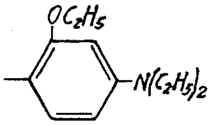
Figure 54:
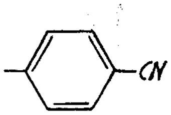
Figure 55:
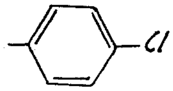
Figure 56:
Figure 57:
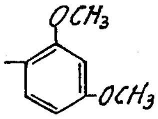

A clear colorless solution of 50.0 mgm of the dihydroheterocyclic amine of FIG. 60 and 5.0 gm VYHH solution (10% by weight VYHH in methylethylketone-toluene solvent; 3 parts methylethylketone, 1 part toluene) was knife coated on a sheet of polyvinylidene fluoride (3 mil or 0.075 mm) to a wet thickness of three mils (0.075 mm) and then dried at room temperature to form a light-stable colorless transparent sheet.

Exposure of the sheet material to a conventional electron beam yields a transparent, sharp magenta image. The magenta image is clearly visible at $10^{12}$ electrons/cm$^2$ and at $10^{14}$ electorns/cm$^2$, the optical density equals one.

EXAMPLE 11

Polyester (2.5 mil or 0.0625 mm) was vapor coated with chromium to yield a sheet material with a resistivity of 10 ohms-cm and a visible light transmission of 50%. A clear colorless solution of 50 mgm each of the dihydroheterocyclic amines of FIGS. 59 and 80 and 5.0 g of a solution of 10% VYHH in 3:1 methylethylketone-toluene solvent was knife coated on the conductive surface of the substrate at a wet thickness of 3 mils (0.075 mm) and dried at room temperature to form a colorless transparent sheet which was stable to room light.

The resulting sheet was exposed to a conventional electron beam using 20kV, 3$\mu$A. The film, upon exposure to the electron beam, immediately developed a sharp transparent purple image. The image was easily defined at $10^{11}$ electrons/cm$^2$. An optical density of one was obtained by an exposure of $5 \times 10^{13}$ electrons/cm$^2$. The imaged sheet was stored under normal room light for one week and then re-exposed to the electron beam on an area of the film which previously had not been struck by the beam. The transparent purple image developed and the optical density of image was essentially the same as the originally developed areas.

EXAMPLE 12

Bond paper (No. 10) was knife coated with a solution of Calgon 261 (4 parts Calgon 261 to 6 parts $H_2O$) to a wet thickness of 3 mils (0.075 mm). The resulting sheet was allowed to dry, but while it was still tacky, it was knife coated with the dye progenitor-binder formulation of Example 11 above. The coated sheet was dried at room temperature to form a light-stable colorless sheet.

Exposure of the sheet to conventional electron beam yields a sharp magenta image at $10^{12}$ electrons/cm$^2$.

EXAMPLE 13

Three separate transparent recording sheets (A, B and C) are preapred in accordance with the procedures described in Example 8, using 2-(5-(1,3,3-trimethylindolylidene-2)penta-1,3-dienyl-1)-1,3,3-trimethylindoline and the specific dihydroheterocyclic amaines of FIGS. 60 and 70 respectively.

A full color picture was mounted horizontally in a rigid frame and a television camera (Concord Separate Mesh Vidicon-Model CTC-30)was focused on the picture. Focusing and centering is observed on a TV monitor. A red filter (peak transmission at 630 m$\mu$) is placed in front of the camera lens and the resulting signal is fed into a 3M Electron Beam Recoder Model 100. Sheet A is used to record the resulting red separation and gives a cyan image. The process is repeated using a green filter which peaks at 525 m$\mu$ and the green separation is recorded on Sheet B to give a magenta image. The process is again repeated using a blue filter which peaks at 450 m$\mu$ and the blue separation is recorded on Sheet C to give a yellow image. The resulting three images are laminated in register, with the yellow image on the bottom, then the cyan and finally the magenta image on the top. The composite is then a full color 16 mm positive transparency of the original 8½ × 11 inch color picture. The transparency was projected to about a 4 × 5 foot size to give a sharp, clear, faithful color reproduction of the original picture.

EXAMPLE 14

Three sheets of polyester were coated with Calgon 261 as described in Example 9. The resulting conductive sheets were coated with dye progenitor-binder systems and exposed to the modulated electron beam as described in Example 13. The three exposed color separations were laminated in register and the resulting positive transparency was projected to give a superior, sharp, brightly colored copy of the original.

EXAMPLE 15

Three sheets of polyester were coated with Calgon 261 as described in Example 9. The first sheet was coated with a mixture of 50.0 mgm of the dihydroheterocyclic amine of FIG. 60 in 5.0 gms of a 10% solution of VYHH in methylethylketone to a wet thickness of 3.0 mils. The resulting sheet yields a magenta image upon exposure to an electron beam.

The second sheet was coated with a mixture of 50.0 mgm of Michler's Hydrol, bis(p-dimethylaminophenyl)carbinol, in 5.0 gms of a 10% solution of VYHH in methylethylketone to a wet thickness of 3.0 mils. The resulting sheet yields a cyan image upon exposure to an electron beam.

The third sheet was coated with 50.0 mgm of 2-(2-(4-carbamidoxyphenyl)ethenyl)-3,3-dimethylindolenine (described in U.S. Pat. No. 3,542,775) in 5.0 gms of a 10% solution of VYHH in methylethylketone. The resulting sheet yields a yellow image upon exposure to an electron beam.

The three sheets are exposed as described in Example 13 and the resulting positive transparency yields a very sharp, faithful projection of the original.

What is claimed is:

1. A N-hydrocarbyl substituted dihydroheterocyclic amine selected from the group consisting of $D-(CH=CH)_nA$ and $D-(CH=CH)_nCH=CAA'$ wherein *n* is an integer from 1–3 inclusive, D is:

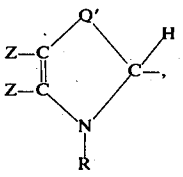

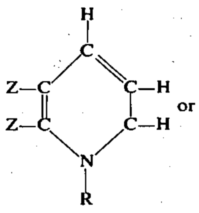

or

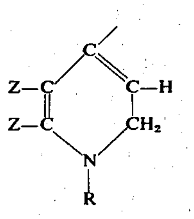

A and A' are independently:

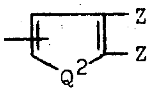

or

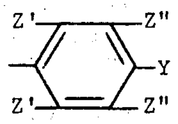

and A and A' when taken together with the carbon to which attached are:

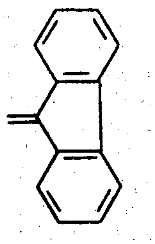

or

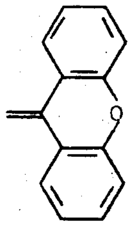

R is hydrocarbyl;

Q' is =CR'R', S, O, Se or =NR';

$Q^2$ is O, S, Se, =NH, or =NR;

Z is hydrogen or taken together with an adjacent Z, the group of two may be either benzo- or naphtho- with or without an auxochromic substituent;

Y is H, Cl, F, Br, alkyl of 1–6 carbon atoms, OH, $OR^2$, $SR^5$ or $NR^3R^4$;

Z' is H, Cl, F, Br, alkyl of 1–6 carbon atoms, —$OR^5$ or —$NR_2^5$;

Z'' is H, Cl, F, Br, alkyl of 1–6 carbon atoms or —$OR^5$; or

Z' and adjacent Z'' taken together can be benzo- or naphto- with or without auxochromic substituents;

R' is H, alkyl of 1–6 carbon atoms; phenyl or benzyl;

$R^2$ is alkyl of 1–6 carbon atoms;

$R^5$ is methyl or ethyl;

$R^3$ and $R^4$ are independently hydrocarbyl or halohydrocarbyl or taken together with an adjacent Z'' each can be independently 1,2-ethylene, 1,3-propylene or 1,2-phenylene or in conjunction with each other can form a 5–6 member ring including not more than 1 oxygen or one additional nitrogen.

2. An N-hydrocarbyl-substituted dihydroheterocyclic amine according to claim 1 wherein R is alkyl of 1–6 carbon atoms and R' is methyl.

3. An N-hydrocarbyl-substituted dihydroheterocyclic amine according to claim 1 having the structure $D-(CH=CH)_n-A$ wherein *n* is an integer from 1 to 3 inclusive, D is:

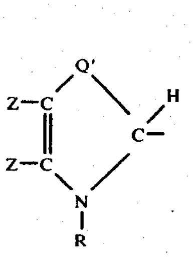
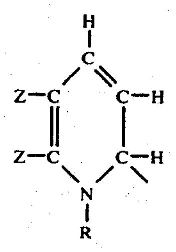
or
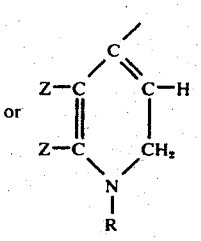

A is:

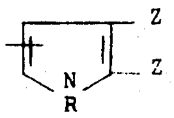
or
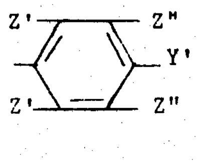

R is alkyl of 1–6 carbon atoms

Q' is CR'R', S, O, Se or NR'

Y' is $NR^6R^7$, N-piperidino or N-morpholino

Z is hydrogen or taken together with an adjacent Z, the group of two may be either benzo- or naphtho- with or without an auxochromic substituent;

Z' is H, Cl, F, Br, alkyl 0f 1–6 carbon atoms, $—OR^5$ or $—NR_2^5$;

Z'' is H, Cl, F, Br, alkyl of 1–6 carbon atoms or $—OR^5$;

Z' and adjacent Z'' taken together can be benzo- or naphtho- with or without auxochromic substituents;

R' is methyl $R^6$ and $R^7$ are independently hydrocarbyl.

4. An N-hydrocarbyl-substituted dihydroheterocyclic amine according to claim 1 having the structure $$D—(CH=CH)_n—CH=CAA'$$

wherein D is:

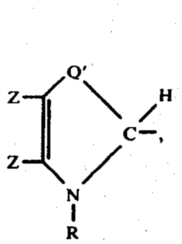
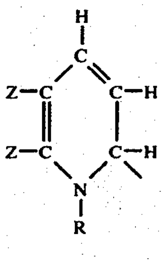
or
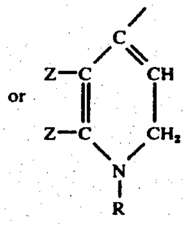

*n* is an integer from 1–3 inclusive;

R is alkyl of 1–6 carbon atoms;

Q' is CR'R', S, O, Se or NR';

R' is methyl; and

A and A' are dimethylaminophenyl or halodimethylaminophenyl.

5. The N-hydrocarbyl-substituted dihydroheterocyclic amine according to claim 3 wherein D is 1,3,3-trimethylindolinyl, *n* is 1 and A is 2-chloro-4-dimethyl amino methylphenyl.

6. The N-hydrocarbyl-substituted dihydroheterocyclic amine according to claim 3 wherein D is 1,3,3-trimethylindolinyl, *n* is 1 and A is 2,4-dimethoxyphenyl.

7. The N-hydrocarbyl-substituted dihydroheterocyclic amine according to claim 3 wherein D is 5-chloro-1,3,3-trimethylindolinyl, *n* is 1 and A is 3-bromo-4-dimethylaminophenyl.

8. The N-hydrocarbyl-substituted heterocyclic amine according to claim 3 wherein D is 1,3,3-trimethylindolinyl, *n* is 1 and A is 4-dimethylaminophenyl.

9. The N-hydrocarbyl-substituted heterocyclic amine according to claim 3 wherein D is 3-ethyl-2,3-dihydro-2-benzothiazolyl, *n* is 1 and A is 4-dimethylamainophenyl.

10. The N-hydrocarbyl-substituted heterocycline amine according to claim 4 wherein D is 1,3,3-trimethylindolinyl, *n* is 1 and A and A' are 4-dimethylaminophenyl.

11. The N-hydrocarbyl-substituted heterocyclic amine according to claim 4 where D is 5-chloro-1,3,3-trimethylindolinyl, *n* is 1 and A and A' are 4-dimethylaminophenyl.

12. An N-hydrocarbyl-substituted dihydroheterocyclic amine according to claim 1 convertible from a colorless state to a colored state by exposure to an ionizing source in the presence of an anionogen.

* * * * *

UNITED STATES PATENT AND TRADEMARK OFFICE

CERTIFICATE OF CORRECTION

PATENT NO. : 3,974,147

DATED : August 10, 1976

INVENTOR(S) : George V. D. Tiers and Joseph A. Wiese, Jr.

It is certified that error appears in the above-identified patent and that said Letters Patent are hereby corrected as shown below:

[56], line 8, "p. 1." should read -- p. 1737-1743. -- .

Column 2, line 27, "or 4-)" should read -- (or 4-) -- .

Column 2, line 35, "," should read -- . -- .

Column 3, line 43, "$NR_2{}^5$" should read -- $NR_2^5$ -- .

Column 3, line 44, "$OR^{5;}$" should read -- $OR^5$; -- .

Column 4, line 21, "...(5-benzo)..." should read -- ...(5,6-benzo)... -- .

Column 11, line 4, "weights" should read -- weighs -- .

Column 12, line 31, "procedure" should read -- procedures -- .

Column 14, line 8, "electorns/$cm^2$" should read -- electrons/$cm^2$ -- .

Column 14, line 31, "had" should read -- has -- .

Column 14, line 50, "preapred" should read -- prepared -

Column 14, line 53, "amaines" should read -- amines -- .

Claim 1, second diagram, second "C-H" should read -- C-H -- .

Column 16, line 48,"$-NR_2{}^5$" should read -- $-NR_2^5$ -- .

UNITED STATES PATENT AND TRADEMARK OFFICE

CERTIFICATE OF CORRECTION

PATENT NO. : 3,974,147

DATED : August 10, 1976

INVENTOR(S) : George V. D. Tiers and Joseph A. Wiese, Jr.

It is certified that error appears in the above-identified patent and that said Letters Patent are hereby corrected as shown below:

Column 17, line 30, "Of" should read -- of -- .

Column 17, line 31, "$-NR_2{}^{5};$" should read -- $-NR^5_2;$ -- .

Column 17, line 33, "$-OR^{5};$" should read -- $-OR^5;$ -- .

Signed and Sealed this

*Thirteenth* Day of *September 1977*

[SEAL]

*Attest:*

RUTH C. MASON
*Attesting Officer*

LUTRELLE F. PARKER
*Acting Commissioner of Patents and Trademarks*